United States Patent
Gehring et al.

[11] Patent Number: 4,681,618
[45] Date of Patent: Jul. 21, 1987

[54] 1-ARYL-5-HALO-4-NITOPYRAZOLES, HERBICIDAL COMPOSITIONS CONTAINING THEM, AND HERBICIDAL METHOD OF USING THEM

[75] Inventors: Reinhold Gehring, Wuppertal; Otto Schallner, Monheim; Jörg Stetter, Wuppertal; Hans-Joachim Santel, Colonge; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 816,643

[22] Filed: Jan. 6, 1986

[30] Foreign Application Priority Data

Jan. 17, 1985 [DE] Fed. Rep. of Germany ....... 3501323

[51] Int. Cl.$^4$ .................... A01N 43/56; C07D 231/16
[52] U.S. Cl. ........................................ 71/92; 548/376
[58] Field of Search ............................ 548/376; 71/92

[56] References Cited

U.S. PATENT DOCUMENTS 3,869,274  3/1975  Crovetti et al. .................... 548/376
4,025,530  5/1977  Crovetti et al. .................... 548/376

FOREIGN PATENT DOCUMENTS 573919  3/1976  Switzerland ........................ 548/376

*Primary Examiner*—Henry R. Jiles
*Assistant Examiner*—Kurt G. Briscoe
*Attorney, Agent, or Firm*—Sprung Horn Kramer & Woods

[57] ABSTRACT

Herbicidally effective 1-aryl-4-nitropyrazoles of the general formula (I)

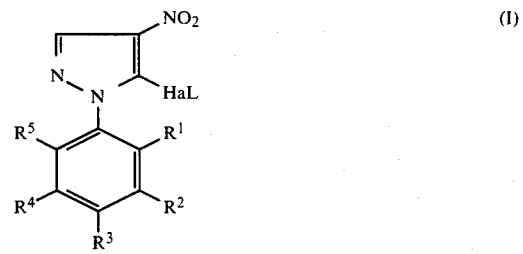

in which
   Hal represents halogen,
   $R^1$ and $R^3$ independently of one another represent cyano, nitro, halogen, alkyl, alkoxy, alkoxycarbonyl, halogenoalkyl, halogenoalkoxy or a radial —S(O)$_n$—R$^6$ and
   $R^2$, $R^4$ and $R^5$ independently of one another and independently of $R^1$ and $R^3$ represent the same radicals as $R^1$ and $R^3$, and additionally represent hydrogen,
and wherein
   $R^6$ represents alkyl, halogenoalkyl, amino, alkylamino or dialkylamino and n-represents the number 0, 1 or 2 are disclosed.

6 Claims, No Drawings

1-ARYL-5-HALO-4-NITROPYRAZOLES, HERBICIDAL COMPOSITIONS CONTAINING THEM, AND HERBICIDAL METHOD OF USING THEM

The invention relates to new 1-aryl-4-nitropyrazoles, several processes for their preparation and their use as herbicides.

It is already known that certain 1-aryl-pyrazoles, such as, for example, 4-cyano-5-propionamido-1-(2,3,4-trichlorophenyl)-pyrazole, have herbicidal properties (see, for example, DE-OS No. (German Published Specification) 3,226,513).

However, the herbicidal activity of these already known compounds towards weeds, like their tolerance towards important crop plants, is not always completely satisfactory in all fields of use.

New 1-aryl-4-nitropyrazoles of the general formula

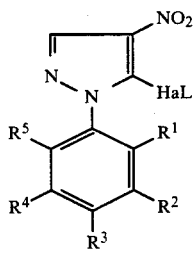

(I)

in which
Hal represents halogen,
$R^1$ and $R^3$ independently of one another represent cyano, nitro, halogen, alkyl, alkoxy, alkoxycarbonyl, halogenoalkyl, halogenoalkoxy or a radical —S(O)$_n$—R$^6$ and
$R^2$, $R^4$ and $R^5$ independently of one another and independently of $R^1$ and $R^3$ represent the same radicals as $R^1$ and $R^3$, and additionally represent hydrogen, and wherein
$R^6$ represents alkyl, halogenoalkyl, amino, alkylamino or dialkylamino and
n represents the number 0, 1 or 2,
have now been found.

It has furthermore been found that the new 1-aryl-4-nitropyrazoles of the general formula (I)

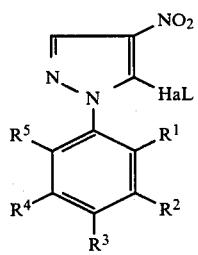

(I)

in which
Hal represents halogen,
$R^1$ and $R^3$ independently of one another represent cyano, nitro, halogen, alkyl, alkoxy, alkoxycarbonyl, halogenoalkyl, halogenoalkoxy or a radical —S(O)$_n$—R$^6$ and
$R^2$, $R^4$ and $R^5$ independently of one another and independently of $R^1$ and $R^3$ represent the same radicals as $R^1$ and $R^3$, and additionally represent hydrogen, and wherein
$R^6$ represents alkyl, halogenoalkyl, amino, alkylamino or dialkylamino and
n represents the number 0, 1 or 2,
are obtained by a process in which
(a) 1-arylpyrazoles of the general formula (II)

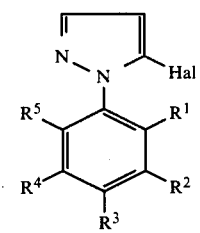

(II)

in which
$R^1$, $R^2$, $R^3$, $R^4$, $R^5$ and Hal have the above-mentioned meaning,
are reacted with nitric acid, if appropriate in the presence of a diluent and if appropriate in the presence of a catalyst, or in which
(b) 5-amino-4-nitropyrazoles of the formula (III)

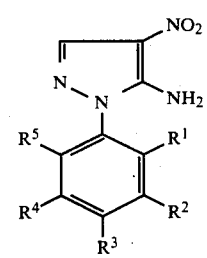

(III)

in which
$R^1$, $R^2$, $R^3$, $R^4$, $R^5$ and Hal have the above-mentioned meaning,
are reacted with nitrite compounds of the formula (IV)

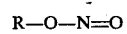

(IV)

in which
R represents hydrogen, an alkali metal cation or alkyl,
and a haloform of the formula (V)

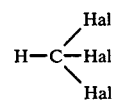

(V)

in which
Hal has the abovementioned meaning,
if appropriate in the presence of a catalyst, or in which
(c) the 1-aryl-4-nitropyrazoles obtainable according to process (a) or (b), of the formula (I)

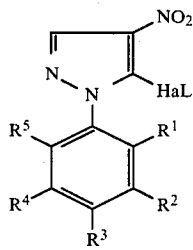

in which

R¹, R², R³, R⁴, R⁵ and Hal have the above-mentioned meaning, are reacted with halides of the formula (VI)

in which

M⊕ represents one equivalent of a metal cation or an optionally substituted ammonium ion and Hal'⊖ represents halogen, but is other than Hal, if appropriate in the presence of a diluent and if appropriate in the presence of a phase transfer catalyst.

In this manner, from a particular halogen derivative of the 1-aryl-4-nitropyrazoles of the formula (I), for example the chlorine derivative, transhalogenation, for example with sodium iodide, gives the corresponding halogen derivatives of the 1-aryl-4-nitropyrazoles of the formula (I) in which, for example, chlorine is replaced by iodine.

Finally, it has been found that the new 1-aryl-4-nitropyrazoles of the general formula (I) have herbicidal properties, and in particular also selective herbicidal properties.

Surprisingly, the 1-aryl-4-nitropyrazoles of the general formula (I) according to the invention, whilst having a comparable generally herbicidal activity against weeds which are difficult to combat, exhibit a considerably improved selectivity towards crop plants in comparison with the 1-arylpyrazoles known from the prior art, such as, for example, 4-cyano-5-propionylamino-1-(2,3,4-trichloro-phenyl)pyrazole, which are closely related compounds chemically and from the point of view of their action.

Formula (I) provides a general definition of the 1-aryl-4-nitropyrazoles according to the invention. Preferred compounds of the formula (I) are those in which Hal represents halogen, R¹ and R³ independently of one another represent cyano, nitro or halogen, or represent in each case straight-chain or branched alkyl, alkoxy or alkoxycarbonyl with in each case 1 to 4 carbon atoms in the alkyl part, or represent in each case straight-chain or branched halogenoalkyl or halogenoalkoxy with in each case 1 to 4 carbon atoms and 1 to 9 identical or different halogen atoms, or represent a radical —S(O)$_n$—R⁶ and R², R⁴ and R⁵ independently of one another and independently of R¹ and R³ represent the same radicals as R¹ and R³ and also represent hydrogen, and wherein R⁶ represents amino, or in each case straight-chain or branched alkyl, alkylamino, dialkylamino or halogenoalkyl with in each case 1 to 4 carbon atoms in the individual alkyl parts and, in the case of halogenoalkyl, with 1 to 9 identical or different halogen atoms and n represents the number 0, 1 or 2.

Particularly preferred compounds of the formula (I) are those in which

Hal represents fluorine, chlorine, bromine or iodine,

R¹ and R³ independently of one another represent cyano, nitro, fluorine, chlorine, bromine, iodine, methyl, ethyl, n- or i-propyl or n-, i-, s- or t-butyl, or represent methoxy, ethoxy, methoxycarbonyl or ethoxycarbonyl, or represent trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl or pentachloroethyl, or represent trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy or pentachloroethoxy, or represent a radical —S(O)$_n$—R⁶ and R², R⁴ and R⁵ independently of one another and independently of R¹ and R³ represent the same radicals as R¹ and R³, and also represent hydrogen, and wherein R⁶ represents amino, methylamino, ethylamino, dimethylamino, diethylamino, fluorodichloromethyl, difluoromethyl, tetrafluoroethyl, trichloroethyl, trifluoromethyl, methyl or ethyl and n represents the number 0, 1 or 2.

The 1-aryl-4-nitropyrazoles of the general formula (I) listed by way of their formulae in the following table may be mentioned specifically, in addition to the compounds mentioned in the preparation examples:

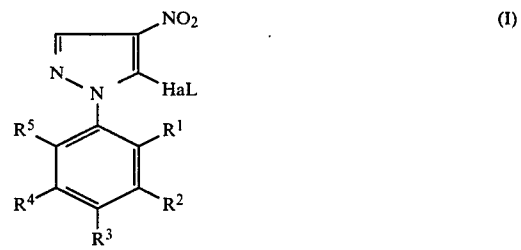

TABLE 1

| Hal | R¹ | R² | R³ | R⁴ | R⁵ |
|-----|-----|-----|-----|-----|-----|
| Cl | Cl | H | Cl | H | H |
| Cl | Cl | Cl | Cl | H | H |
| Cl | Cl | H | Cl | H | Cl |
| Cl | NO₂ | H | NO₂ | H | H |
| Cl | Cl | H | CF₃ | H | H |
| Cl | Cl | H | CF₃ | H | Cl |
| Cl | CF₃ | H | CF₃ | H | H |
| Cl | Cl | Cl | CF₃ | H | Cl |
| Cl | Cl | Cl | Cl H | Cl | |
| Cl | Cl | H | OCF₃ | H | H |
| Cl | Cl | H | OCF₃ | H | Cl |
| Cl | Cl | H | SCF₃ | H | H |
| Cl | Cl | H | SCF₃ | H | Cl |
| Cl | Cl | Cl | SCF₃ | H | H |
| Cl | Cl | Cl | SCF₃ | H | Cl |
| Cl | F | F | OCF₃ | H | F |
| Cl | F | F | OCF₃ | F | F |
| Cl | Cl | Cl | OCF₃ | H | H |
| Cl | Br | H | SCF₃ | H | H |
| Cl | Br | H | OCF₃ | H | Br |
| Cl | NO₂ | H | NO₂ | H | NO₂ |
| Cl | F | H | OCF₃ | H | F |
| Cl | F | H | CF₃ | H | F |

TABLE 1-continued

| Hal | $R^1$ | $R^2$ | $R^3$ | $R^4$ | $R^5$ |
|---|---|---|---|---|---|
| Cl | F | F | SCF$_3$ | H | F |
| Cl | F | H | SCF$_3$ | H | F |
| Cl | I | H | OCF$_3$ | H | H |
| Cl | Cl | H | SO$_2$CF$_3$ | H | Cl |
| Cl | CF$_3$ | H | CF$_3$ | H | CF$_3$ |
| Cl | CF$_3$ | H | SO$_2$CF$_3$ | H | CF$_3$ |
| Cl | CF$_3$ | H | SCF$_3$ | H | CF$_3$ |
| Cl | CF$_3$ | H | SCF$_3$ | H | H |
| Cl | Br | H | CF$_3$ | H | Br |
| Cl | F | F | SO$_2$CF$_3$ | H | F |
| Cl | Cl | Cl | SCF$_3$ | Cl | Cl |
| Cl | Cl | F | Cl | H | Cl |
| Cl | F | F | F | F | F |
| Cl | F | F | CF$_3$ | F | F |
| Cl | Cl | Cl | Cl | Cl | Cl |
| Cl | Cl | H | SO$_2$CH$_3$ | H | Cl |
| Cl | Cl | Cl | SO$_2$CF$_3$ | H | H |
| Cl | Br | H | SO$_2$CF$_3$ | H | Br |
| Cl | NO$_2$ | H | CF$_3$ | H | H |
| Cl | F | H | SO$_2$CF$_3$ | H | F |
| Cl | Cl | H | OCH$_3$ | H | Cl |
| Cl | Cl | H | SCH$_3$ | H | Cl |
| Cl | F | H | F | H | F |
| Cl | Cl | H | SO$_2$CH$_3$ | H | H |
| Cl | Cl | H | SO$_2$CH$_3$ | H | Cl |
| Cl | Cl | H | SO$_2$CClF$_2$ | H | Cl |
| Cl | Br | H | OCF$_3$ | H | H |
| Cl | Br | H | SCF$_3$ | H | Br |
| Cl | Br | H | Br | H | Br |
| Cl | Br | H | Br | H | H |
| Cl | Br | H | Cl | H | Cl |
| Cl | Cl | H | Br | H | Cl |
| Cl | Cl | H | Br | H | Br |
| Cl | Cl | H | SO$_2$CF$_3$ | H | H |
| Cl | Cl | H | SO$_2$CF$_2$Cl | H | H |
| Cl | Cl | H | SO$_2$CF$_2$Cl | H | Cl |
| Cl | Br | H | SO$_2$CF$_2$Cl | H | H |
| Cl | Cl | H | OCF$_2$Cl | H | H |
| Cl | Cl | H | OCF$_2$Cl | H | Cl |
| Cl | Cl | H | OCF$_2$CHF$_2$ | H | Cl |
| Cl | Cl | H | CF$_2$Cl | H | Cl |
| Cl | Cl | H | OCF$_2$Cl | H | H |
| Cl | Cl | H | OCHF$_2$ | H | H |
| Cl | Cl | H | OCHF$_2$ | H | Cl |
| Cl | Cl | H | OCH$_2$CF$_3$ | H | H |
| Cl | Cl | H | OCH$_2$CF$_3$ | H | Cl |
| Cl | Cl | H | OCF$_2$CHFCl | H | H |
| Cl | Cl | H | OCF$_2$CHFCl | H | Cl |
| Cl | Cl | H | CHF$_2$ | H | Cl |
| Cl | Cl | H | CHF$_2$ | H | H |
| Cl | Br | H | OCH$_2$CF$_3$ | H | Br |
| Cl | Br | H | OCH$_2$CF$_3$ | H | H |
| Cl | Br | H | SO$_2$CF$_2$Cl | H | H |
| Cl | Br | H | SO$_2$CF$_2$Cl | H | Br |
| Cl | Br | H | SO$_2$CH$_3$ | H | H |
| Cl | Br | H | SO$_2$CH$_3$ | H | Br |
| Br | Cl | H | Cl | H | H |
| Br | Cl | Cl | Cl | H | H |
| Br | Cl | H | Cl | H | Cl |
| Br | NO$_2$ | H | NO$_2$ | H | H |
| Br | Cl | H | CF$_3$ | H | H |
| Br | Cl | H | CF$_3$ | H | Cl |
| Br | CF$_3$ | H | CF$_3$ | H | H |
| Br | Cl | Cl | CF$_3$ | H | Cl |
| Br | Cl | Cl | Cl | H | Cl |
| Br | Cl | H | OCF$_3$ | H | H |
| Br | Cl | H | OCF$_3$ | H | Cl |
| Br | Cl | H | SCF$_3$ | H | H |
| Br | Cl | H | SCF$_3$ | H | Cl |
| Br | Cl | Cl | SCF$_3$ | H | H |
| Br | Cl | Cl | SCF$_3$ | H | Cl |
| Br | F | F | OCF$_3$ | H | F |
| Br | F | F | OCF$_3$ | F | F |
| Br | Cl | Cl | OCF$_3$ | H | H |
| Br | Br | H | SCF$_3$ | H | H |
| Br | Br | H | OCF$_3$ | H | Br |
| Br | NO$_2$ | H | NO$_2$ | H | NO$_2$ |
| Br | F | H | OCF$_3$ | H | F |
| Br | F | H | CF$_3$ | H | F |
| Br | F | F | SCF$_3$ | H | F |
| Br | F | H | SCF$_3$ | H | F |
| Br | I | H | OCF$_3$ | H | H |
| Br | Cl | H | SO$_2$CF$_3$ | H | Cl |
| Br | CF$_3$ | H | CF$_3$ | H | CF$_3$ |
| Br | CF$_3$ | H | SO$_2$CF$_3$ | H | CF$_3$ |
| Br | CF$_3$ | H | SCF$_3$ | H | CF$_3$ |
| Br | CF$_3$ | H | SCF$_3$ | H | H |
| Br | Br | H | CF$_3$ | H | Br |
| Br | F | F | SO$_2$CF$_3$ | H | F |
| Br | Cl | Cl | SCF$_3$ | Cl | Cl |
| Br | Cl | F | Cl | H | Cl |
| Br | F | F | F | F | F |
| Br | F | F | CF$_3$ | F | F |
| Br | Cl | Cl | Cl | Cl | Cl |
| Br | Cl | H | SO$_2$CH$_3$ | H | Cl |
| Br | Cl | Cl | SO$_2$CF$_3$ | H | H |
| Br | Br | H | SO$_2$CF$_3$ | H | Br |
| Br | NO$_2$ | H | CF$_3$ | H | H |
| Br | F | H | SO$_2$CF$_3$ | H | F |
| Br | Cl | H | OCH$_3$ | H | Cl |
| Br | Cl | H | SCH$_3$ | H | Cl |
| Br | F | H | F | H | F |
| Br | Cl | H | SO$_2$CH$_3$ | H | H |
| Br | Cl | H | SO$_2$CH$_3$ | H | Cl |
| Br | Cl | H | SO$_2$CClF$_2$ | H | Cl |
| Br | Br | H | OCF$_3$ | H | H |
| Br | Br | H | SCF$_3$ | H | Br |
| Br | Br | H | Br | H | Br |
| Br | Br | H | Br | H | H |
| Br | Cl | H | Br | H | Cl |
| Br | Cl | H | Br | H | Br |
| Br | Cl | H | SO$_2$CF$_3$ | H | H |
| Br | Cl | H | SO$_2$CF$_2$Cl | H | H |
| Br | Cl | H | SO$_2$CF$_2$Cl | H | Cl |
| Br | Br | H | SO$_2$CF$_2$Cl | H | H |
| Br | Cl | H | OCF$_2$Cl | H | H |
| Br | Cl | H | OCF$_2$Cl | H | Cl |
| Br | Cl | H | OCF$_2$CHF$_2$ | H | Cl |
| Br | Cl | H | CF$_2$Cl | H | Cl |
| Br | Cl | H | OCF$_2$Cl | H | H |
| Br | Cl | H | OCHF$_2$ | H | H |
| Br | Cl | H | OCHF$_2$ | H | Cl |
| Br | Cl | H | OCH$_2$CF$_3$ | H | H |
| Br | Cl | H | OCH$_2$CF$_3$ | H | Cl |
| Br | Cl | H | OCF$_2$CHFCl | H | H |
| Br | Cl | H | OCF$_2$CHFCl | H | Cl |
| Br | Cl | H | CHF$_2$ | H | Cl |
| Br | Cl | H | CHF$_2$ | H | H |
| Br | Br | H | OCH$_2$CF$_3$ | H | Br |
| Br | Br | H | OCH$_2$CF$_3$ | H | H |
| Br | Br | H | SO$_2$CF$_2$Cl | H | H |
| Br | Br | H | SO$_2$CF$_2$Cl | H | Br |
| Br | Br | H | SO$_2$CH$_3$ | H | H |
| Br | Br | H | SO$_2$CH$_3$ | H | Br |
| F | Cl | H | Cl | H | H |
| F | Cl | H | Cl | H | Cl |
| F | NO$_2$ | H | NO$_2$ | H | H |
| F | Cl | H | CF$_3$ | H | H |
| F | Cl | H | CF$_3$ | H | Cl |
| F | CF$_3$ | H | CF$_3$ | H | H |
| F | Cl | Cl | CF$_3$ | H | Cl |
| F | Cl | Cl | Cl | H | Cl |
| F | Cl | H | OCF$_3$ | H | H |
| F | Cl | H | OCF$_3$ | H | Cl |
| F | Cl | H | SCF$_3$ | H | H |
| F | Cl | H | SCF$_3$ | H | Cl |
| F | Cl | Cl | SCF$_3$ | H | H |
| F | Cl | Cl | SCF$_3$ | H | Cl |
| F | F | F | OCF$_3$ | H | F |
| F | F | F | OCF$_3$ | F | F |
| F | Cl | Cl | OCF$_3$ | H | H |
| F | Br | H | SCF$_3$ | H | H |
| F | Br | H | OCF$_3$ | H | Br |
| F | NO$_2$ | H | NO$_2$ | H | NO$_2$ |
| F | F | H | OCF$_3$ | H | F |
| F | F | H | CF$_3$ | H | F |
| F | F | F | SCF$_3$ | H | F |
| F | F | H | SCF$_3$ | H | F |
| F | I | H | OCF$_3$ | H | H |
| F | Cl | H | SO$_2$CF$_3$ | H | Cl |

TABLE 1-continued

| Hal | R¹ | R² | R³ | R⁴ | R⁵ |
|---|---|---|---|---|---|
| F | CF₃ | H | CF₃ | H | CF₃ |
| F | CF₃ | H | SO₂CF₃ | H | CF₃ |
| F | CF₃ | H | SCF₃ | H | CF₃ |
| F | CF₃ | H | SCF₃ | H | H |
| F | Br | H | CF₃ | H | Br |
| F | F | F | SO₂CF₃ | H | F |
| F | Cl | Cl | SCF₃ | Cl | Cl |
| F | Cl | F | Cl | H | Cl |
| F | F | F | F | F | F |
| F | F | F | CF₃ | F | F |
| F | Cl | Cl | Cl | Cl | Cl |
| F | Cl | H | SO₂CH₃ | H | Cl |
| F | Cl | Cl | SO₂CF₃ | H | H |
| F | Br | H | SO₂CF₃ | H | Br |
| F | NO₂ | H | CF₃ | H | H |
| F | F | H | SO₂CF₃ | H | F |
| F | Cl | H | OCH₃ | H | Cl |
| F | Cl | H | SCH₃ | H | Cl |
| F | F | H | F | H | F |
| F | Cl | H | SO₂CH₃ | H | H |
| F | Cl | H | SO₂CH₃ | H | Cl |
| F | Cl | H | SO₂CClF₂ | H | Cl |
| F | Br | H | OCF₃ | H | H |
| F | Br | H | SCF₃ | H | Br |
| F | Br | H | Br | H | Br |
| F | Br | H | Br | H | H |
| F | Br | H | Cl | H | Cl |
| F | Cl | H | Br | H | Cl |
| F | Cl | H | Br | H | Br |
| F | Cl | H | SO₂CF₃ | H | H |
| F | Cl | H | SO₂CF₂Cl | H | H |
| F | Cl | H | SO₂CF₂Cl | H | Cl |
| F | Br | H | SO₂CF₂Cl | H | H |
| F | Cl | H | OCF₂Cl | H | H |
| F | Cl | H | OCF₂Cl | H | Cl |
| F | Cl | H | OCF₂CHF₂ | H | Cl |
| F | Cl | H | CF₂Cl | H | Cl |
| F | Cl | H | OCF₂Cl | H | H |
| F | Cl | H | OCHF₂ | H | H |
| F | Cl | H | OCHF₂ | H | Cl |
| F | Cl | H | OCH₂CF₃ | H | H |
| F | Cl | H | OCH₂CF₃ | H | Cl |
| F | Cl | H | OCF₂CHFCl | H | H |
| F | Cl | H | OCF₂CHFCl | H | Cl |
| F | Cl | H | CHF₂ | H | Cl |
| F | Cl | H | CHF₂ | H | H |
| F | Br | H | OCH₂CF₃ | H | Br |
| F | Br | H | OCH₂CF₃ | H | H |
| F | Br | H | SO₂CF₂Cl | H | H |
| F | Br | H | SO₂CF₂Cl | H | Br |
| F | Br | H | SO₂CH₃ | H | H |
| F | Br | H | SO₂CH₃ | H | Br |
| I | Cl | H | Cl | H | H |
| I | Cl | Cl | Cl | H | H |
| I | Cl | H | Cl | H | Cl |
| I | NO₂ | H | NO₂ | H | H |
| I | Cl | H | CF₃ | H | H |
| I | Cl | H | CF₃ | H | Cl |
| I | CF₃ | H | CF₃ | H | H |
| I | Cl | Cl | CF₃ | H | Cl |
| I | Cl | Cl | Cl | H | Cl |
| I | Cl | H | OCF₃ | H | H |
| I | Cl | H | OCF₃ | H | Cl |
| I | Cl | H | SCF₃ | H | H |
| I | Cl | H | SCF₃ | H | Cl |
| I | Cl | Cl | SCF₃ | H | H |
| I | Cl | Cl | SCF₃ | H | Cl |
| I | F | F | OCF₃ | H | F |
| I | F | F | OCF₃ | F | F |
| I | Cl | Cl | OCF₃ | H | H |
| I | Br | H | SCF₃ | H | H |
| I | Br | H | OCF₃ | H | Br |
| I | NO₂ | H | NO₂ | H | NO₂ |
| I | F | H | OCF₃ | H | F |
| I | F | H | CF₃ | H | F |
| I | F | F | SCF₃ | H | F |
| I | F | H | SCF₃ | H | F |
| I | I | H | OCF₃ | H | H |
| I | Cl | H | SO₂CF₃ | H | Cl |
| I | CF₃ | H | CF₃ | H | CF₃ |
| I | CF₃ | H | SO₂CF₃ | H | CF₃ |
| I | CF₃ | H | SCF₃ | H | CF₃ |
| I | CF₃ | H | SCF₃ | H | H |
| I | Br | H | CF₃ | H | Br |
| I | F | F | SO₂CF₃ | H | F |
| I | Cl | Cl | SCF₃ | Cl | Cl |
| I | Cl | F | Cl | H | Cl |
| I | F | F | F | F | F |
| I | F | F | CF₃ | F | F |
| I | Cl | Cl | Cl | Cl | Cl |
| I | Cl | H | SO₂CH₃ | H | Cl |
| I | Cl | Cl | SO₂CF₃ | H | H |
| I | Br | H | SO₂CF₃ | H | Br |
| I | NO₂ | H | CF₃ | H | H |
| I | F | H | SO₂CF₃ | H | F |
| I | Cl | H | OCH₃ | H | Cl |
| I | Cl | H | SCH₃ | H | Cl |
| I | F | H | F | H | F |
| I | Cl | H | SO₂CH₃ | H | H |
| I | Cl | H | SO₂CH₃ | H | Cl |
| I | Cl | H | SO₂CClF₂ | H | Cl |
| I | Br | H | OCF₃ | H | H |
| I | Br | H | SCF₃ | H | Br |
| I | Br | H | Br | H | Br |
| I | Br | H | Br | H | H |
| I | Br | H | Cl | H | Cl |
| I | Cl | H | Br | H | Cl |
| I | Cl | H | Br | H | Br |
| I | Cl | H | SO₂CF₃ | H | H |
| I | Cl | H | SO₂CF₂Cl | H | H |
| I | Cl | H | SO₂CF₂Cl | H | Cl |
| I | Br | H | SO₂CF₂Cl | H | H |
| I | Cl | H | OCF₂Cl | H | H |
| I | Cl | H | OCF₂Cl | H | Cl |
| I | Cl | H | OCF₂CHF₂ | H | Cl |
| I | Cl | H | CF₂Cl | H | Cl |
| I | Cl | H | OCF₂Cl | H | H |
| I | Cl | H | OCHF₂ | H | H |
| I | Cl | H | OCHF₂ | H | Cl |
| I | Cl | H | OCH₂CF₃ | H | H |
| I | Cl | H | OCH₂CF₃ | H | Cl |
| I | Cl | H | OCF₂CHFCl | H | H |
| I | Cl | H | OCF₂CHFCl | H | Cl |
| I | Cl | H | CHF₂ | H | Cl |
| I | Cl | H | CHF₂ | H | H |
| I | Br | H | OCH₂CF₃ | H | Br |
| I | Br | H | OCH₂CF₃ | H | H |
| I | Br | H | SO₂CF₂Cl | H | H |
| I | Br | H | SO₂CF₂Cl | H | Br |
| I | Br | H | SO₂CH₃ | H | H |
| I | Br | H | SO₂CH₃ | H | Br |

If, for example, 5-chloro-1-(2,4,6-trichlorophenyl)-pyrazole and nitric acid are used as starting substances, the course of the reaction in process (a) according to the invention can be represented by the following equation:

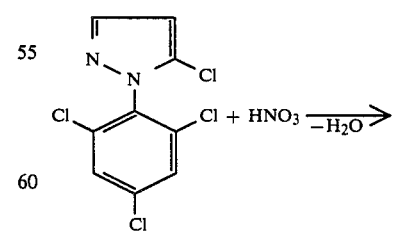

-continued

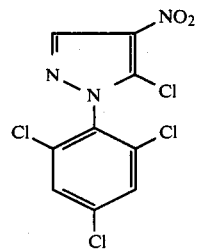

If, for example, 5-amino-4-nitro-1-(2,4,6-trichlorophenyl)-pyrazole, t-butyl nitrite and bromoform are used as starting substances, the course of the reaction in process (b) according to the invention can be represented by the following equation:

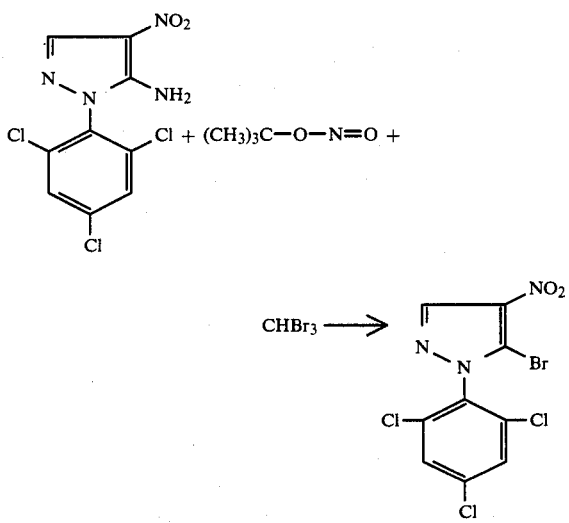

If, for example, 5-chloro-4-nitro-1-(2,3,4-trichlorophenyl)-pyrazole and sodium iodide are used as starting substances, the course of the reaction in process (c) according to the invention can be represented by the following equation:

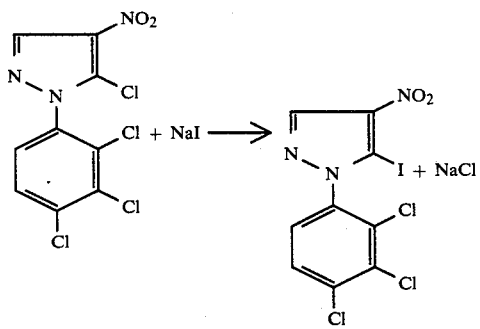

Formula (II) provides a general definition of the 1-arylpyrazoles required as starting substances for carrying out process (a) according to the invention. In this formula (II), $R^1$, $R^2$, $R^3$, $R^4$, $R^5$ and Hal preferably represent those radicals which have already been mentioned as preferred for these substituents in connection with the description of the substances of the formula (I) according to the invention.

The 1-arylpyrazoles of the formula (II) are not yet known. They are obtained by a process in which alkoxymethylenemalonates of the formula (VII)

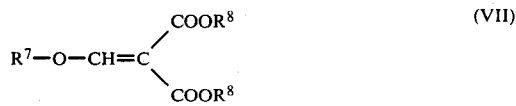

in which
$R^7$ and $R^8$ independently of one another in each case represent alkyl, in particular methyl or ethyl,
are initially reacted with phenylhydrazines of the formula (VIII)

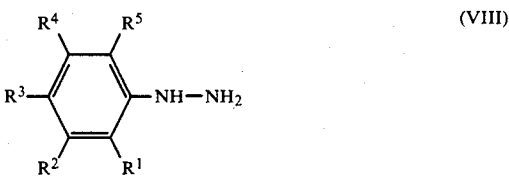

in which
$R^1$, $R^2$, $R^3$, $R^4$ and $R^5$ have the abovementioned meaning,
in a first stage, if appropriate in the presence of a diluent, such as, for example, methanol or ethanol, at temperatures between +10° C. and +80° C. If appropriate, the intermediate product which intermediately occurs here, of the formula (VIIIa)

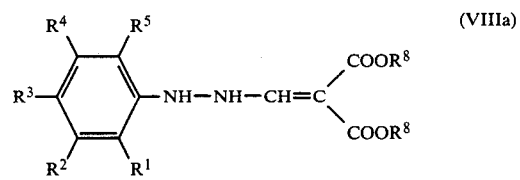

in which
$R^1$, $R^2$, $R^3$, $R^4$, $R^5$ and $R^8$ have the above-mentioned meaning,
can also be isolated and cyclised in a separate reaction stage.

The pyrazolecarboxylic acid esters thus obtainable, of the formula (IX)

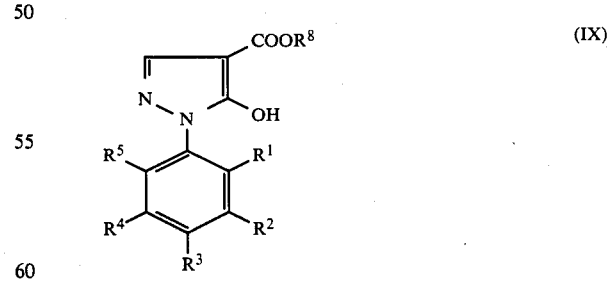

in which
$R^1$, $R^2$, $R^3$, $R^4$, $R^5$ and $R^8$ have the above-mentioned meaning,
are decarboxylated in a 2nd stage, if appropriate in the presence of a diluent, such as, for example, methanol, and if appropriate in the presence of a base, such as, for example, sodium hydroxide, at temperatures between 30° C. and 70° C. and the pyrazolinones thus obtainable, of the formula (X)

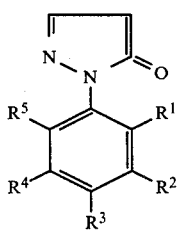

in which
R¹, R², R³, R⁴ and R⁵ have the abovementioned meaning,
are then reacted with halogenating agents, such as, for example, phosphorus oxychloride or phosphorus oxybromide, in a 3rd stage by customary known processes (see, for example, Ber. dtsch. chem. Ges. 28, 35 [1895] or Liebigs Ann. Chem. 373, 129 [1910]).

If appropriate, the cyclisation and subsequent decarboxylation can also be carried out in one reaction stage as a "one-pot process" (see, for example, Liebigs Ann. Chem. 373, 142 (1910) and the preparation examples).

The alkoxymethylenemalonates of the formula (VII) are generally known compounds of organic chemistry.

The phenylhydrazines of the formula (VIII) are known in most cases, or they can be prepared by known processes in a simple analogous manner (see, for example, Houben-Weyl "Methoden der organischen Chemie" ("Methods of Organic Chemistry") Volume X, 2, page 203, Thieme Verlag Stuttgart 1967), for example by a process in which the known anilines of the formula (XI)

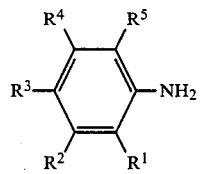

in which
R¹, R², R³, R⁴ and R⁵ have the abovementioned meaning,
are reacted with sodium nitrite in the presence of an acid, such as, for example, sulfuric acid, and then with tin(II) chloride, likewise in the presence of an acid, such as, for example, hydrochloric acid, at temperatures between −20° C. and +80° C., or, alternatively, the known chlorobenzenes of the formula (XIa)

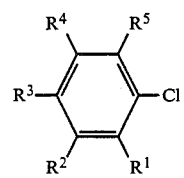

in which
R¹, R², R³, R⁴ and R⁵ have the abovementioned meaning, are reacted with hydrazine hydrate, if appropriate in the presence of a diluent, such as, for example, dioxane, at temperatures between 20° C. and 150° C.

Formula (III) provides a general definition of the 5-amino-4-nitropyrazoles required as starting substances for carrying out process (b) according to the invention. In this formula, R¹, R², R³, R⁴ and R⁵ preferably represent those substituents which have already been mentioned as preferred for these radicals in connection with the description of the substances of the formula (I) according to the invention.

The 5-amino-4-nitropyrazoles of the formula (III) are likewise not yet known. However, they are the subject of a previous not published Patent Application which has been filed by the Applicant Company (German Pat. No. 3,402,308 of 24.01.1984).

They are obtained, for example, by a process in which phenylhydrazines of the formula (VIII)

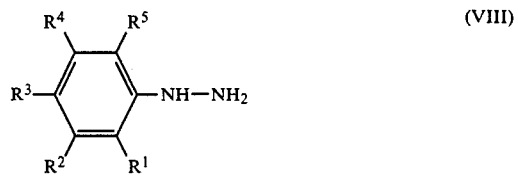

in which
R¹, R², R³, R⁴ and R⁵ have the abovementioned meaning,
are reacted either with acrylonitrile derivatives of the formula (XII)

in which
A represents halogen, hydroxyl or alkoxy, in particular chlorine, bromine, hydroxyl, methoxy or ethoxy,
or with 2-halogenoacrylonitriles of the formula (XIIa)

in which
Hal" represents halogen, in particular chlorine or bromine,
or with 2,3-dihalogenopropionitriles of the formula (XIIb)

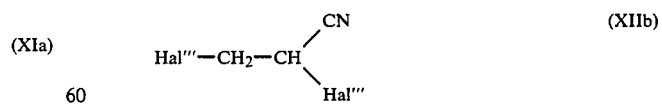

in which
Hal''' represents halogen, in particular chlorine or bromine,
initially in one stage, if appropriate in the presence of a diluent, such as, for example, methanol, and if appropriate in the presence of a reaction auxiliary, such as, for example, acetic acid, at temperatures between −20° C.

and +20° C., to give the phenylhydrazines of the formula (XIII)

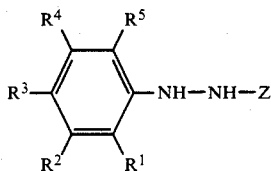

in which
R$^1$, R$^2$, R$^3$, R$^4$ and R$^5$ have the abovementioned meaning and
Z represents one of the radicals

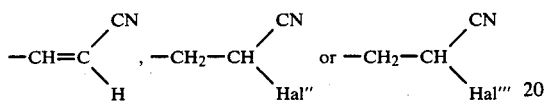

wherein
Hal" and Hal'" have the above mentioned meaning and represent identical or different halogen atoms,
and these are cyclised in a 2nd stage, if appropriate in the presence of a diluent, such as, for example, methanol, and if appropriate in the presence of an acid-binding agent, such as, for example, sodium carbonate, at temperatures between +50° C. and +150° C., or are cyclised directly in one reaction step, without isolation of the intermediate stage of the formula (XIII), if appropriate in the presence of a diluent, such as, for example, methanol, at temperatures between +50° C. and +150° C., to give the 5-amino-pyrazoles of the formula (XIV)

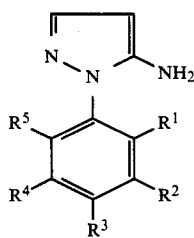

in which
R$^1$, R$^2$, R$^3$, R$^4$ and R$^5$ have the abovementioned meaning,
and these are nitrated in a 3rd stage with nitric acid, if appropriate in the presence of a diluent, such as, for example, acetic acid, and if appropriate in the presence of a catalyst, such as, for example, acetic anhydride, at temperatures between −20° C. and +150° C.

The acrylonitrile derivatives of the formula (XII) are known (see, for example, DE-OS No. (German Published Specification) 3,129,429, European Pat. No. 34,945; J. Chem. Soc. D 1970, 1255; Can. J. Chem. 48, 2104–2109 (1970), J. Heterocyclic Chem. 19, 1267–1273 (1982); and Can. J. Chem. 51, 1239–1244 (1973)), or they can be obtained by processes which are known from the literature, in a simple analogous manner.

The 2-halogenoacrylonitriles of the formula (XIIa) and the 2,3-dihalogeno-propionitriles of the formula (XIIb) are likewise known (see, for example, J. Prakt. Chem. 321, 93 [1979], J. Heterocyclic Chem. 19, 1265 [1982]; and J. Heterocyclic Chem. 19, 1267 [1982]).

Formula (IV) provides a general definition of the nitrite compounds furthermore required as starting substances for carrying out process (b) according to the invention. In this formula, R preferably represents hydrogen, or represents a sodium or potassium cation, or represents straight-chain or branched alkyl with 1 to 4 carbon atoms.

The nitrite compounds of the formula (IV) are generally known basic chemicals.

Formula (V) provides a general definition of the haloforms furthermore required as starting substances for carrying out process (b) according to the invention. In this formula (V), Hal preferably represents chlorine, bromine or iodine.

The haloforms of the formula (V) are likewise generally known compounds of organic chemistry.

The compounds according to the invention of the 1-aryl-4-nitropyrazoles of the formula (I) which are obtainable with the aid of processes (a) and (b) according to the invention are employed as starting substances in carrying out process (c) according to the invention.

Formula (VI) provides a general definition of the halides furthermore required as starting substances for carrying out process (c) according to the invention. In this formula (VI), M$^\oplus$ preferably represents a sodium or potassium cation, or represents an ammonium or tetraalkylammonium ion, possibly alkyl radicals being those with 1 to 12 carbon atoms. Hal' represents fluorine, chlorine, bromine or iodine.

The halides of the formula (VI) are likewise generally known compounds of organic chemistry.

Possible diluents for carrying out process (a) according to the invention are all the solvents-which-can usually be employed for such nitration reactions. The acids possible as reagents or mixtures thereof with catalyst acid, such as, for example, sulfuric acid, nitric acid, acetic anhydride or nitrating acid, are preferably simultaneously used as the diluents. If appropriate, inert organic solvents, such as, for example, glacial acetic acid or chlorinated hydrocarbons, such as methylene chloride, chloroform or carbon tetrachloride, are also possible diluents.

Possible catalysts or reaction auxiliaries for carrying out process (a) according to the invention are likewise the catalysts usual for such nitrations; acid catalysts, such as, for example, sulfuric acid or acetic anhydride, are preferably used.

The reaction temperatures can be varied within a substantial range in carrying out process (a) according to the invention. In general, the reaction is carried out between −50° C. and +200° C., preferably between −20° C. and +150° C.

For carrying out process (a) according to the invention, in general 1.0 to 100 moles, preferably 1.0 to 50 moles, of nitric acid and, if appropriate, 0.1 to 10 moles of catalyst are employed per mole of 1-arylpyrazole of the formula (II).

The reaction is carried out and the reaction products of the formula (I) are worked up and isolated in the generally customary manner.

Possible diluents for carrying out process (b) according to the invention are all the solvents which can usually be employed for such diazotisation reactions, such as, for example, acetic acid or dioxane. A corresponding excess of the haloform simultaneously employed as a reactant is preferably used as the diluent. A corresponding excess of a catalyst acid which can be used, if appropriate, can also simultaneously be employed in the diluent.

Possible catalysts for carrying out process (b) according to the invention are all the catalysts customary for such diazotisation reactions. Acids, such as, for example, hydrochloric acid, hydrobromic acid or sulfuric acid, are preferably used.

The reaction temperatures can be varied within certain ranges for carrying out process (b) according to the invention. In general, the reaction is carried out between $-20°$ C. and $+120°$ C., preferably between $0°$ C. and $+80°$ C.

For carrying out process (b) according to the invention, in general 1.0 to 100 moles of haloform of the formula (V) and 1.0 to 10 moles of nitrite of the formula (IV) are employed per mole of 5-amino-4-nitropyrazole of the formula (III). The reaction is carried out and the reaction products are worked up and isolated analogously to known processes (see, for example, "Organikum" 15th edition, VEB Deutscher Verlag der Wissenschaften Berlin 1981, page 652 et seq. or J. Chem. Soc. C 1966, 1249 or Rev. Latinoam. Quim. 13, 100-102 (1982)).

Possible diluents for carrying out process (c) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, sulfoxides or sulfones, such as dimethylsulfoxide or sulfolane, or alcohols, such as methanol, ethanol or propanol.

Possible catalysts for carrying out process (c) according to the invention are quaternary ammonium or phosphonium salts of cyclic polyethers.

Examples which may be mentioned of such catalysts are: tetrabutylammonium iodide, tetrabutylammonium bromide, tributylmethylphosphonium bromide, trimethyl-$C_{13}$/$C_{15}$-alkylammonium chloride, dibenzyldimethyl-ammonium-methyl sulfate, dimethyl-$C_{12}$/$C_{14}$-alkyl-benzylammonium chloride, tetrabutylammonium hydroxide, 18-crown-6, triethylbenzylammonium chloride and trimethylbenzylammonium chloride.

The reaction temperature can be varied within a substantial range in carrying out process (c) according to the invention. It is in general between $0°$ C. and $+120°$ C., preferably between $+20°$ C. and $+80°$ C.

For carrying out process (c) according to the invention, in general 1.0 to 50 moles, preferably 1.0 to 20 moles, of halide of the formula (VI) and 0.01 to 1.0 moles of phase transfer catalyst are employed per mole of starting compound of the formula (I). The reaction is carried out and the reaction products are worked up and isolated analogously to known processes (see, for example, "Organikum", 15th edition, VEB Deutscher Verlag der Wissenschaften Berlin 1981, page 421 et seq.).

Processes (a), (b) and (c) according to the invention are in general carried out under normal pressure. However, it is also possible for them to be carried out under increased or reduced pressure.

Besides being used as herbicidal active compounds, the compounds of the formula (I) according to the invention can also be used as intermediate products for the synthesis of further active compounds. For example, they can be reacted with amines to give the corresponding 5-amino-1-aryl-4-nitropyrazoles, which are likewise herbicidally active and are the subject of a previous patent application which has been filed by the Applicant Company (see German Pat. No. 3,402,308 of 24.01.1984).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

Besides having a particularly good generally herbicidal activity, the active compounds of the formula (I) according to the invention also exhibit a considerably improved selectivity towards crop plants in important crops and can be employed as agents for selectively combating weeds in dicotyledon crops, such as, for example, sugar beet, cotton plantations, soya beans or groundnuts, and also in monocotyledon crops, in particular cereals, such as, for example, wheat.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulfoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulfonates, alkylsulfates, arylsulfonates as well as albumin hydrolyzation products; as dispersing agents there are suitable: for example lignin-sulfate waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one, for combating weeds in sugar beet, and 4-amino-6-(1,1-dimethylethyl)-3-methylthio-1,2,4-triazin-5(4H)-one, for combating weeds in soya bean.

Mixtures with heteroaryl-oxyacetamides; N,N-dimethyl-N'-(3-chloro-4-methylphenyl)-urea, N,N-dimethyl-N'-(4-isopropylphenyl)-urea, 4-amino-6-t-butyl-3-ethylthio-1,2,4-triazin-5(4H)-one, 2,4-dichlorophenoxyacetic acid, 2,4-dichlorophenoxypropionic acid, (2-methyl-4-chlorophenoxy)acetic acid, (4-chloro-2-methyl-phenoxy)-propionic acid, chloroacetic acid N-(methoxymethyl)-2,6-diethylanilide, O-(methoxycarbonylaminophenyl) N-phenyl-carbamate; 2,6-dinitro-4-trifluoromethyl-N,N-dipropylaniline, 2-ethoxy-2,3-dihydro-3,3-dimethyl-5-benzofuranyl methanesulfonate; butyl-2-<4-[(5-trifluoromethyl-2-pyridinyl)-oxy]-phenoxy>-propanoate; S-(2,3,3-trichloroallyl)-N,N-diisopropyl-thiocarbamate; 5-amino-4-chloro-2-phenyl-2,3-dihydro-3-oxo-pyridazine; methyl-6,6-dimethyl-2,4-dioxo-3-[1-(2-propenyloxyamino)butylidene]-cyclohexanecarboxylic acid; 3,5-diiodo-4-hydroxybenzonitrile; 3-isopropyl-2,1,3-benzothiadiazin-4-one 2,2-dioxide; 2-chloro-N-[4-methoxy-6-methyl-1,3,5-triazin-2-yl)-aminocarbonyl]-benzenesulfonamide; 4-ethylamino-2-t-butylamino-6-methylthio-s-triazine; N-(1-ethylpropyl)-3,4-dimethyl-2,6-dinitroaniline and 2-<4-[(3-chloro-5-trifluoromethyl-2-pyridinyl)-oxy]-phenoxy>-propanoic acid and -propanoic acid ethyl ester are also possible. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.01 and 5 kg per ha.

The preparation and use of the active compounds according to the invention can be seen from the following examples.

PREPARATION EXAMPLES

EXAMPLE 1 according to process (a)

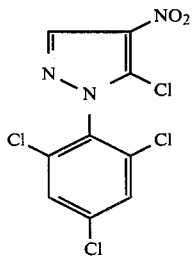

26 ml (0.62 mole) of fuming nitric acid are added dropwise to a suspension of 7.0 g (0.025 mole) of 5-chloro-1-(2,4,6-trichlorophenyl)-pyrazole in 30 ml of acetic anhydride at room temperature in the course of 2.5 hours, with stirring, such that the internal temperature does not rise above 35° C. (about 10 ml/hour). When the addition has ended, the mixture is subsequently stirred at room temperature for 1 hour and poured onto ice-water, the oily product is taken up in chloroform, the mixture is washed in each case twice with saturated sodium carbonate solution and water and dried over sodium sulphate and the solvent is removed in vacuo. The crystalline residue is digested with petroleum ether, filtered off with suction and dried.

6.0 g (b 73% of theory) of 5-chloro-4-nitro-1-(2,4,6-trichlorophenyl)-pyrazole of melting point 78° C.–84° C. are obtained.

EXAMPLE 2 according to process (b)

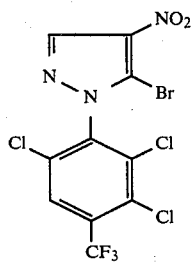

4.8 ml (0.04 mole) of t-butyl nitrite are added dropwise to 5.2 g (0.014 mole) of 5-amino-4-nitro-1-(2,3,6-trichloro-4-trifluoromethylphenyl)-pyrazole in 16 ml (0.18 mole) of bromoform in the course of 10 minutes, with stirring, during which the temperature of the reaction mixture rises to 50° C. When the addition has ended, the mixture is stirred at the reflux temperature for a further hour and concentrated in vacuo and the oil which remains is purified by column chromatography (silica gel/eluant: chloroform/acetone 9:1).

5.0 g (82% of theory) of 5-bromo-4-nitro-1-(2,3,6-trichloro-4-trifluoromethylphenyl)-pyrazole of melting point 97° C.–99° C. are obtained.

The 1-aryl-4-nitropyrazoles of the general formula (I) listed in the following table are obtained in a corresponding manner and according to the general preparation information:

TABLE 2

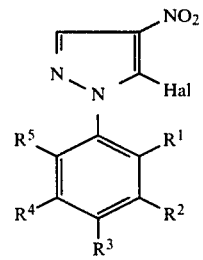

| Example No. | Hal | $R^1$ | $R^2$ | $R^3$ | $R^4$ | $R^5$ | Melting point (°C.) |
|---|---|---|---|---|---|---|---|
| 3 | Cl | Cl | H | $CF_3$ | H | Cl | 82–84 |
| 4 | Cl | Cl | H | $OCF_3$ | H | H | 64–70 |
| 5 | Br | Cl | H | $CF_3$ | H | Cl | 96 |
| 6 | Br | Cl | H | $CF_3$ | H | Br | 89–97 |
| 7 | Br | $OCF_3$ | H | Br | H | Br | 86 |
| 8 | Br | Cl | H | $SO_2CF_3$ | H | Cl | 142–144 |
| 9 | Br | Cl | H | $CF_3$ | H | H | oil |
| 10 | Br | Cl | Cl | $SCF_3$ | H | Cl | oil |
| 11 | Br | Cl | H | $OCF_3$ | H | H | 83 |
| 12 | Br | Cl | Cl | $OCF_3$ | H | Cl | oil |

PREPARATION OF THE STARTING COMPOUNDS

EXAMPLE II-1

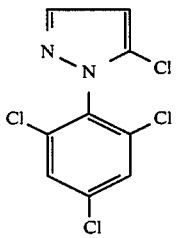

200 g (0.76 mole) of 1-(2,4,6-trichlorophenyl)-4H-$\Delta^2$-pyrazolin-5-one are heated together with 500 ml (837.5 g=2.95 moles) of phosphorus oxychloride at 160° C. in an autoclave for 16 hours. For working up, the cooled reaction mixture is poured onto ice and stirred for 15 minutes, the precipitate is filtered off with suction and rinsed with water and, for purification, the residue is stirred in concentrated aqueous ammonia solution at about 40° C. for 0.5 hours, filtered off with suction again, rinsed with water and dried. For further purification, the dry powder is dissolved in chloroform, the solution is washed with water, the chloroform phase is dried over sodium sulphate and the solvent is removed in vacuo.

118 g (55% of theory) of 5-chloro-1-(2,4,6-trichlorophenyl)-pyrazole of melting point 96° C. are obtained.

The 1-aryl-5-halogenopyrazoles of the general formula (II) listed in the following table are obtained in a corresponding manner and according to the general preparation information:

TABLE 3

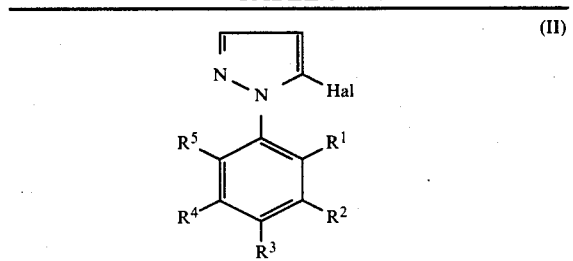

| | | |
|---|---|---|
| Example II-2 | 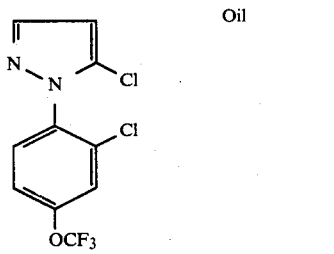 | Oil |
| Example II-3 | 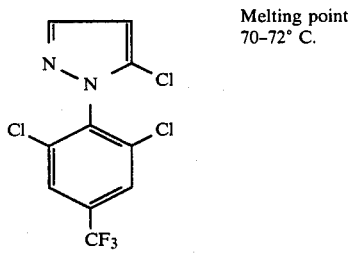 | Melting point 70–72° C. |
| Example III-1 | 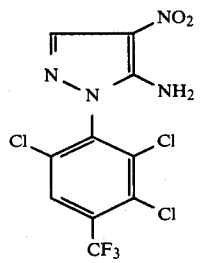 | |

7.5 g (0.0227 mole) of 5-amino-1-(2,3,6-trichloro-4-trifluoromethylphenyl)-pyrazole (see Example XIV-1) and 2.2 ml (2.3 g=0.023 mole) of acetic anhydride in 20 ml of glacial acetic acid are stirred at room temperature for about 4 hours until the starting substance can no longer be detected in the thin-layer chromatogram. A further 2.7 ml (2.9 g=0.0288 mole) of acetic anhydride and, at 5° C. to 10° C., 1.2 ml (1.8 g=0.028 mole) of 98 percent strength nitric acid are then added, the mixture is stirred at room temperature for 8 hours, the solvent is removed in vacuo and the residue is taken up in 30 ml of ethanol and 20 ml of concentrated hydrochloric acid.

The mixture is heated at the reflux temperature for 12 hours and concentrated in vacuo, the residue is taken up in 100 ml of methylene chloride, the mixture is washed carefully (evolution of $CO_2$) with 100 ml of saturated sodium bicarbonate solution and dried over magnesium sulphate and the solvent is removed in vacuo.

7.5 g (84% of theory) of 5-amino-4-nitro-1-(2,3,6-trichloro-4-trifluoromethylphenyl)-pyrazole of melting point 78° C. to 85° C. are obtained.

EXAMPLE VIII-1

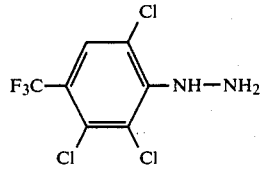

200 g (0.704 mole) of 1,2,3,4-tetrachloro-5-trifluoromethylbenzene and 240 ml (247.2 g/4.94 moles) of hydrazine hydrate in 500 ml of dioxane are heated under reflux for 14 hours. The heavier (aqueous) phase is removed from the cooled two-phase reaction mixture and the organic phase is concentrated to dryness in vacuo. The residue is suspended in 600 ml of water and 100 ml of methylene chloride, the pH is brought to 10 with 10 percent strength aqueous sodium hydroxide solution and the mixture is warmed slowly to 30° C. to 35° C., two clear phases forming from the cloudy suspension. The mixture is allowed to cool to room temperature, the organic phase is separated off, washed with 200 ml of concentrated aqueous sodium chloride solution and dried over magnesium sulfate and the solvent is removed in vacuo. The crude product is stirred in boiling hexane for 3 to 4 hours, the mixture is then cooled at 0° C. to 5° C. for 15 hours and the product is filtered off cold with suction and dried in vacuo at 50° C. for 2 to 3 hours.

146 g (71.2% of theory) of 2,3,6-trichloro-4-trifluoromethyl-phenylhydrazine of melting point 67°–70° C. with a content, determined by gas chromatography, of 96% are obtained.

The following compounds are obtained in a corresponding manner or according to the general preparation information:

EXAMPLE VIII-2

F₃CO—⟨⟩—NH—NH₂ (2-Cl)

Melting point 35° C.

EXAMPLE VIII-3

F₃C—⟨⟩—NH—NH₂ (2,6-diCl)

Melting point 56–57° C.

EXAMPLE VIIIa-1

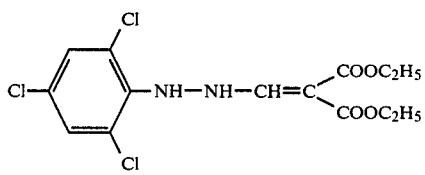

105 g (0.5 mole) of 2,4,6-trichlorophenylhydrazine and 108 g (0.5 mole) of diethyl ethoxymethylenemalonate are heated under reflux in 500 ml of ethanol for 5 hours, the mixture is then stirred at room temperature for 12 hours and subsequently cooled to $-10°$ C. and the residue is filtered off and dried.

N-[2,2-Bis-(ethoxycarbonyl)-vinyl]-N'-(2,4,6-trichlorophenyl)-hydrazine of melting point 92° C. is obtained.

The following compounds are obtained in a corresponding manner:

EXAMPLE VIIIa-2

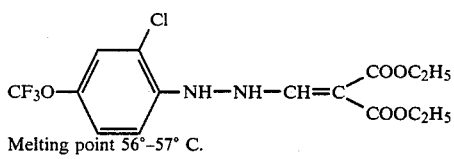

Melting point 56°–57° C.

EXAMPLE VIIIa-3

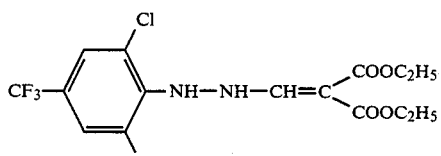

Melting point 77°–83° C.

EXAMPLE IX-1

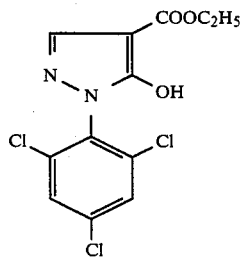

35.8 g (0.094 mole) of N-[2,2-bis(ethoxycarbonyl)-vinyl]-N'-(2,4,6-trichlorophenyl)-hydrazine are slowly heated to 170° C. and are stirred at 170° C. to 175° C. for 45 minutes, during which 11 ml of ethanol are simultaneously distilled off and the residue slowly solidifies.

The residue obtained is stirred with acetonitrile and filtered off with suction.

26 g (82.4% of theory) of 4-ethoxycarbonyl-5-hydroxy-1-(2,4,6-trichlorophenyl)-pyrazole of melting point 228° C. are obtained.

The following compound is obtained in a corresponding manner:

EXAMPLE IX-2

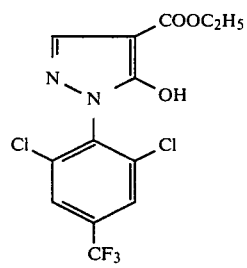

Melting point 188° C.

EXAMPLE X-1

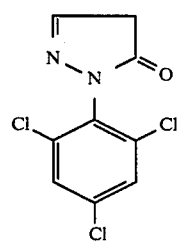

3 g (0.075 mole) of sodium hydroxide—dissolved in 3 ml of water—are added to 5 g (0.015 mole) of 4-ethoxycarbonyl-5-hydroxy-1-(2,4,6-trichlorophenyl)-pyrazole in 75 ml of ethanol and the mixture is heated under reflux for 12 hours; the mixture is allowed to cool, a further 3 g (0.075 mole) of sodium hydroxide, dissolved in 3 ml of water, are added and the mixture is heated at the reflux temperature for another 12 hours. When the starting substance can no longer be detected in the thin-layer chromatogram, the mixture is acidified with concentrated hydrochloric acid and heated again at the reflux temperature for 3 hours, the reaction mixture obtained is filtered, the filtrate is concentrated, the residue is taken up in chloroform, the mixture is washed with water and dried over sodium sulphate and the solvent is removed in vacuo.

1 g (25.3% of theory) of 1-(2,4,6-trichlorophenyl)-4H-$\Delta^2$-pyrazolin-5-one of melting point 202° C. is obtained. (Alternative preparation possibility)

100 g (0.26 mole) of N-[2,2-bis(ethoxycarbonyl)-vinyl]-N'-(2,4,6-trichlorophenyl)-hydrazine and ⓡg (5 moles) of sodium hydroxide are refuxed in 1,400 ml of water for 12 hours. The cooled reaction mixture is carefully acidified with concentrated hydrochloric acid while stirring vigorously (evolution of $CO_2$) and the solid which has precipitated is filtered off with suction and dried in air. It can be recrystallised from ethanol.

53 g (77% of theory) of 1-(2,4,6-trichloropheny)-4H-$\Delta^2$-pyrazolin-5-one of melting point 202° C. are obtained.

The following pyrazolinones of the formula (X) are obtained in a corresponding manner and according to the general preparation information:

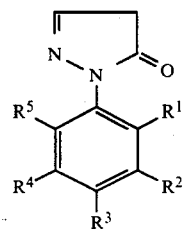

(X)

EXAMPLE X-2

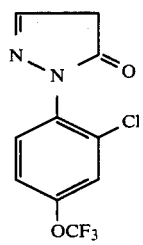

Melting point
210° C. (decomposition)

EXAMPLE X-3

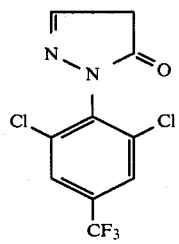

Melting point
228° C.-230° C.

EXAMPLE XIV-1

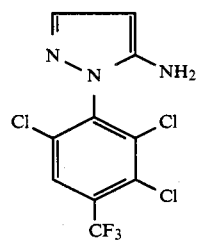

57 ml (62.7 g=0.71 mole) of 2-chloroacrylonitrile are added dropwise to 45 g (0.17 mole) of 2,3,6-trichloro-4-trifluoromethyl-phenylhydrazine and 35 mg (0.1 mmol) of disodium ethylenediaminetetraacetate (Titriplex III) in 260 ml of methanol at the reflux temperature in the course of 30 minutes, and the mixture is stirred at the reflux temperature (about 65° C.) for a further 5 hours. The reaction mixture is concentrated in vacuo, the residue is taken up in 260 ml of methanol, and 15.4 ml (0.541 mole) of concentrated sulfuric acid are added dropwise at room temperature in the course of 15 minutes, with stirring. The temperature of the reaction mixture thereby rises to 32° C. When the addition has ended, the mixture is stirred at 55° C. for 30 hours and cooled to room temperature, 56 g (0.534 mole) of sodium carbonate are added, the mixture is stirred again at room temperature for 4 hours and concentrated in vacuo, the residue is taken up in 550 ml of methylene chloride, 55 ml of water are added, the mixture is stirred at room temperature for 8 hours, the organic phase is separated off, washed with 250 ml of concentrated aqueous sodium chloride solution and dried over magnesium sulphate and the solvent is removed in vacuo.

52.6 g (94% of theory) of 5-amino-1-(2,3,6-trichloro-4-trifluoromethyl-phenyl)-pyrazole of melting point 109° C.-114° C. are obtained.

PREPARATION OF SECONDARY PRODUCTS

EXAMPLE (III-2)

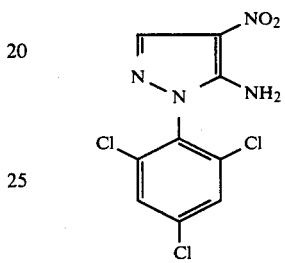

2.8 g (0.0086 mole) of 5-chloro-4-nitro-1-(2,4,6-trichlorophenyl)-pyrazole are heated at 160° C. in 100 ml of ammonia-saturated ethanol in a bomb tube or autoclave for 10 hours. The cooled reaction mixture is concentrated, the residue is taken up in chloroform and the mixture is washed with water, dried over sodium sulfate and concentrated in vacuo. The crystalline residue is recrystallised from toluene.

2.2 g (85% of theory) of 5-amino-4-nitro-1-(2,4,6-trichlorophenyl)-pyrazole of melting point 218° C.-220° C. are obtained.

Use Examples:

The compound shown below was employed as the comparison substance in the following use examples:

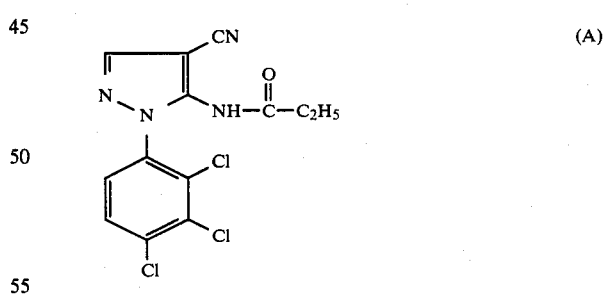

(A)

4-Cyano-5-propionamido-1-(2,3,4-trichloro-phenyl)-pyrazole (known from DE-OS No. (German Published Specification) No. 3,226,513).

EXAMPLE A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, a clear superiority in selectivity towards useful plants in comparison with the prior art is shown, for example, by the compound according to the preparation example: (3)

EXAMPLE B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, a clear superiority in selectivity towards useful plants in comparison with the prior art is shown, for example, by the compound according to the following preparation example: (3)

We claim:

1. A 1-aryl-4-nitropyrazole of the formula (I),

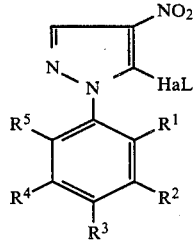

in which
Hal represents halogen,
$R^1$ and $R^3$ independently of one another represent cyano, or halogen, or represent in each case straight-chain or branched alkyl, alkoxy or alkoxy-carbonyl with in each case 1 to 4 carbon atoms, or represent in each case straight-chain or branched halogenoalkyl or halogenoalkoxy with in each case 1 to 4 carbon atoms and 1 to 9 identical or different halogen atoms, or represent a radical —S(O)$_n$—R$^6$ and
$R^2$, $R^4$ and $R^5$ independently of one another and independently of $R^1$ and $R^3$ represent the same radicals as $R^1$ and $R^3$ and also represent hydrogen,
and wherein
$R^6$ represents amino, or in each case straight-chain or branched alkyl, alkylamino, dialkylamino or halogenoalkyl with in each case 1 to 4 carbon atoms in the individual alkyl parts and, in the case of halogenoalkyl, with 1 to 9 identical or different halogen atoms and
n represents the number 0, 1 or 2.

2. A 1-aryl-4-nitropyrazole of the formula (I) according to claim 1, in which
Hal represents fluorine, chlorine, bromine or iodine,
$R^1$ and $R^3$ independently of one another represent cyano, fluorine, chlorine, bromine, iodine, methyl, ethyl, n- or i-propyl or n-, i-, s- or t-butyl, or represent methoxy, ethoxy, methoxycarbonyl or ethoxycarbonyl, or represent trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl or pentachloroethyl, or represent trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy or pentachloroethoxy, or represent a radical —S(O)$_n$—R$^6$ and
$R^2$, $R^4$ and $R^5$ independently of one another and independently of $R^1$ and $R^3$ represent the same radicals as $R^1$ and $R^3$, and also represent hydrogen,
and wherein
$R^6$ represents amino, methylamino, ethylamino, dimethylamino, diethylamino, fluorodichloromethyl, difluoromethyl, tetrafluoroethyl, trichloroethyl, trifluoromethyl, methyl or ethyl and
n represents the number 0, 1 or 2.

3. A 1-aryl-4-nitropyrazole according to claim 2 wherein Hal represents bromine, $R^1$, $R^2$ and $R^5$ represent chlorine, $R^3$ represents trifluoromethyl and $R^4$ represents hydrogen.

4. A herbicidal composition containing a herbicidally effective amount of at least one 1-aryl-4-nitropyrazole of the formula (I) according to claim 1 and an extender and/or surface-active substance.

5. A herbicidal composition containing a herbicidally effective amount of the 1-aryl-4-nitropyrazole according to claim 3 and an extender and/or surface-active substance.

6. A method of combatting weeds, wherein a herbicidally effective amount of a 1-aryl-4-nitro-pyrazole of the formula (I) according to claim 1 is applied to the weeds and/or their environment.

* * * * *

UNITED STATES PATENT AND TRADEMARK OFFICE
CERTIFICATE OF CORRECTION

PATENT NO. : 4,681,618

DATED : July 21, 1987

INVENTOR(S) : Reinhold Gehring, et al.

It is certified that error appears in the above-identified patent and that said Letters Patent is hereby corrected as shown below:

| | |
|---|---|
| Title and Col. 1, line 2 | Correct spelling of --NITROPYRAZOLES-- |
| Title Page, "Abstract", line 3; Col. 1, lines 24, 52; Col. 3, line 5; Col. 4, line 40; Col. 27, line 52 | Top right of formula delete "HaL" and substitute --Hal-- |
| Col. 4, Table 1, line 9 under "$R^3$" | Delete "ClH" and substitute --Cl-- |
| Col. 4, Table 1, line 9 under "$R^4$" | Delete "Cl" and substitute --H-- |
| Col. 4, Table 1, line 9 under "$R^5$" | Insert --Cl-- |
| Col. 14, line 39 | Delete "diluents" and substitute --diluent-- |
| Col. 15, line 1 | Delete "in" and substitute --as-- |
| Col. 15, line 42 | Delete "of" and substitute --or-- |
| Col. 17, line 43 | Delete "sulfate" and substitute -- -sulfite-- |
| Col. 19, line 30 | Before "73%" delete "b" |
| Col. 24, line 54 | Delete "Ⓡ g" and substitute --200 g-- |

Signed and Sealed this

Fifth Day of April, 1988

Attest:

DONALD J. QUIGG

Attesting Officer    Commissioner of Patents and Trademarks